United States Patent [19]

Vantard

[11] Patent Number: 4,655,742

[45] Date of Patent: Apr. 7, 1987

[54] PROCESS/APPARATUS FOR THE WITHDRAWAL/RETURN OF BODY FLUIDS

[75] Inventor: Georges Vantard, Villefontaine, France

[73] Assignee: Rhone-Poulenc S.A., Courbevoie, France

[21] Appl. No.: 631,219

[22] Filed: Jul. 16, 1984

[30] Foreign Application Priority Data

Jul. 13, 1983 [FR] France ............................... 83 11932

[51] Int. Cl.⁴ ............................................. A61M 37/00
[52] U.S. Cl. ..................................... 604/6; 210/195.2; 210/257.2; 210/433.2; 210/651
[58] Field of Search ............... 604/6; 210/195.2, 257.2, 210/321.1, 433.2, 650–651, 927, 90, 97; 128/DIG. 3; 494/6

[56] References Cited

U.S. PATENT DOCUMENTS

| | | |
|---|---|---|
| 2,766,907 | 10/1956 | Wallace, Jr. |
| 4,086,924 | 5/1978 | Latham, Jr. ............................... 604/6 |
| 4,191,182 | 3/1980 | Popovich et al. ....................... 604/6 |
| 4,285,464 | 8/1981 | Latham, Jr. ............................... 604/6 |
| 4,350,156 | 9/1982 | Malchesky et al. .................... 604/6 |

FOREIGN PATENT DOCUMENTS

| | | |
|---|---|---|
| 2100209 | 5/1972 | Fed. Rep. of Germany . |
| 2745041 | 4/1978 | Fed. Rep. of Germany . |
| 2939213 | 5/1980 | Fed. Rep. of Germany . |
| 3043682 | 7/1981 | Fed. Rep. of Germany . |
| 2195483 | 3/1974 | France . |
| 2198759 | 4/1974 | France . |
| WO79/00358 | 12/1979 | PCT Int'l Appl. . |
| WO81/00334 | 10/1981 | PCT Int'l Appl. . |
| WO83/00020 | 6/1982 | PCT Int'l Appl. .................. 210/651 |

Primary Examiner—C. Fred Rosenbaum
Assistant Examiner—Jerome R. Smith, Jr.
Attorney, Agent, or Firm—Burns, Doane, Swecker & Mathis

[57] ABSTRACT

Process/apparatus for the processing of body fluids, advantageously comprising plasmapheresis technique for the fractionation of whole blood, features (i) means, e.g., a common blood transfusion needle, for withdrawing and returning body fluid from and to a living patient, (ii) a body fluid separating module which comprises an upstream first compartment and a downstream second compartment, and having a semipermeable membrane body fluid separator disposed therebetween, (iii) first conduit means communicating said withdrawal and return means (i) with the upstream first compartment of said separating module (ii), (iv) means provided along said first conduit (iii) for conveying body fluid in either direction therein, (v) means adapted to monitor the pressure of body fluid circulating in said first conduit (iii), and provided between said conveying means (iv) and the inlet end of the upstream first compartment of said separating module (ii), (vi) second conduit means communicating the upstream first compartment of said separating module (ii) to (vii) means for flexibly containing body fluid which has not been transported across the semipermeable membrane thereof, (viii) means for collecting body fluid transported across said semipermeable membrane and communicating with the downstream second compartment of said separating module (ii), (ix) means adapted to monitor the amount of body fluid withdrawn from the patient during any given withdrawal phase, and (x) means adapted to expel body fluid from said container means (vii) and to return same to the patient.

23 Claims, 3 Drawing Figures

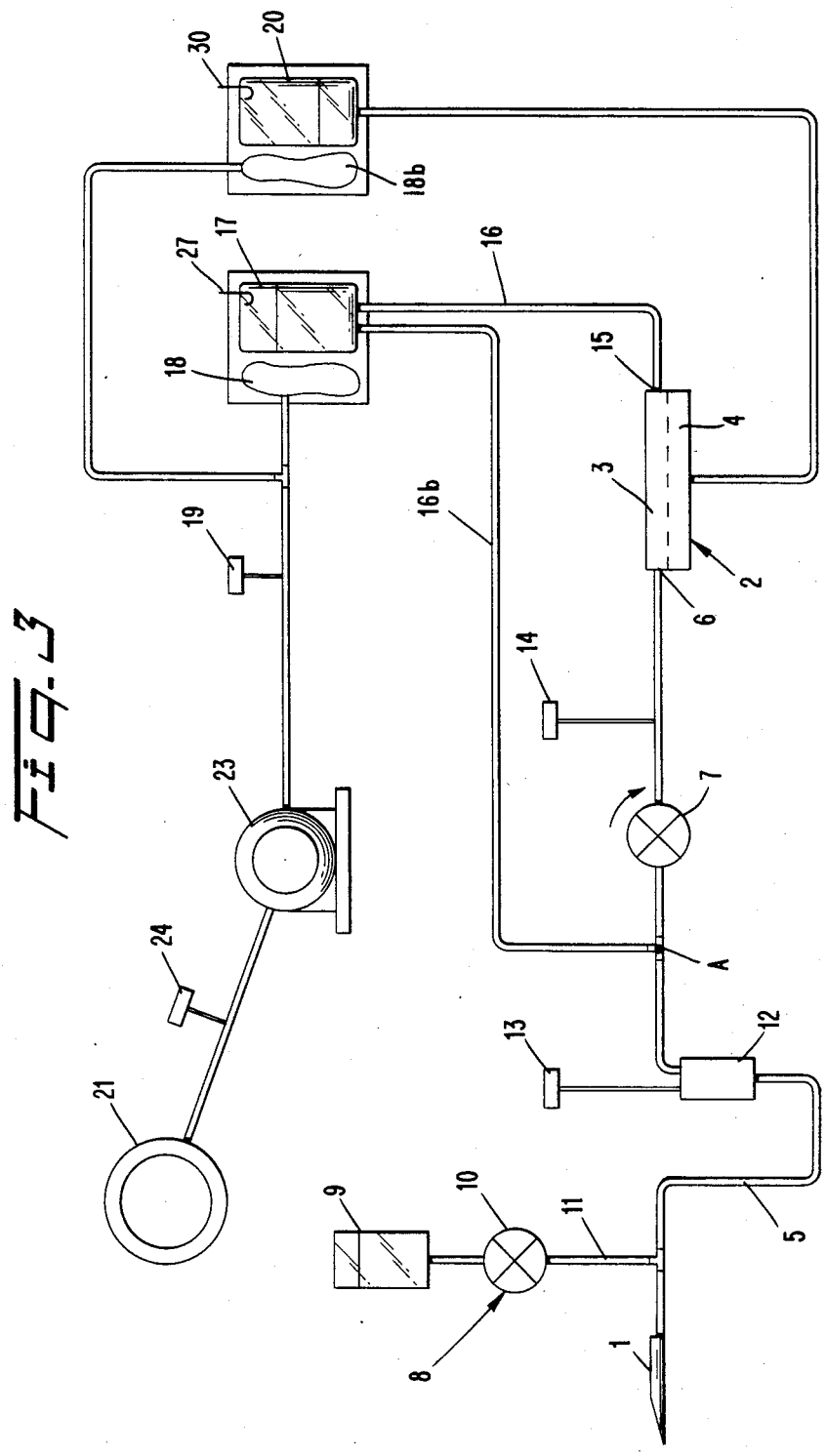

PROCESS/APPARATUS FOR THE WITHDRAWAL/RETURN OF BODY FLUIDS

BACKGROUND OF THE INVENTION

1. Field of the Invention:

The present invention relates to novel plasmapheresis technique, and, more especially, to novel plasmapheresis process/apparatus for the withdrawal/return of body fluid from/to a patient and requiring but a single needle injection therefor.

2. Description of the Prior Art:

Plasmapheresis is a known technique entailing separating the whole blood of a donor into two fractions, the first fraction constituting the plasma phase, while the second fraction constitutes the cellular phase which is typically reinjected back into the donor. The plasma phase is a complex aqueous solution containing protein in particular, while the cellular phase, still containing some of the plasma, comprises the red blood cells (or erythrocytes), the white blood cells (or leucocytes) and the blood platelets.

The technique of plasmapheresis has long been used for animal experimentation. Compare, for example, John J. Abel et al, "Plasma Removal with Return of Corpuscles", which appeared in 1914 in *J. Pharmacol. Exp. Ther.*, No. 5, pages 625 to 641, in which dog's blood is centrifuged to effect the separation. Cf. the article by A. Geiger which appeared in 1931 in *J. Phys.*, 71, pages 111–120, entitled "Method of Ultrafiltration in vivo", in which there is described a continuous plasmapheresis procedure on a dog, the separation apparatus used including a membrane-containing separator, the membrane being arranged in a spiral and being selected in such fashion as to enable a plasma solution to be obtained which contained the totality of the proteins in the treated blood, if so desired.

Plasmapheresis has also been used in man for a number of years, as indicated by the article "La plasmapherese - Technique - Indications" by Fr. Oberling et al, *J. Med. Strasbourg*, pp. 227–279 (March, 1968). Plasmapheresis is thus tending to now supercede the total donation of blood since the former technique has the advantage of permitting larger quantities of plasma to be withdrawn from the patient without drawback or disadvantage. Since the elements formed are restored to the donor, the withdrawal sessions can follow each other at shorter time intervals than when blood in its entirety is donated.

Thus, plasmapheresis is a technique of long standing and the subsequent improvements therein concern either centrifugation-based apparatus or membrane-containing apparatus. Among the several improvement patents relating to membrane-containing apparatus, compare Amicon's German Pat. No. 2,100,209 in which is described a container comprising a membrane forming a spiral for the circulation of whole blood withdrawn from a donor and in which pressure is exerted on the blood contained in the container, either by means of a gas, or by means of a syringe plunger subjected to the action of a leaf spring. By comparison with the apparatus of Geiger described above, this apparatus has, on account of its design, the disadvantage of not permitting continuous operation on the patient. U.S. Pat. No. 4,191,182 describes a membrane-containing apparatus and in which the blood continuously withdrawn from the donor is separated into plasma and a cellular fraction which is continuously returned to the donor, this apparatus having as one particular characteristic the ability to allow one portion of the cellular fraction to recirculate in an upstream compartment of the membrane-containing component and the ability to allow the plasma fraction to recirculate in a downstream compartment of the same component. In published International Application No. wo 79/01,121, apparatus is also described which entails permitting the withdrawal of blood from the donor and the reinjection into the donor of the fraction which has not crossed the membrane, in continuous fashion.

However, each apparatus hereinbefore described as allowing continuous plasmapheresis, nonetheless has the particular disadvantage of requiring insertion of a needle into the patient/donor at two different sites, which is obviously rather unpleasant for him.

SUMMARY OF THE INVENTION

Accordingly, a major object of the present invention is the provision of improved plasmapheresis process/apparatus comprising a membrane-containing module which permits, in particular, plasmapheresis procedures to be performed on the donor by injecting a needle at but a single site, using a conventional blood transfusion needle.

Another object of the present invention is improved plasmapheresis process/apparatus enabling the blood from the donor to be subjected to a first separation upon traversing/contacting the separatory membrane comprising the membrane-containing module while travelling in a direction away from the patient, and then to a second separation by again traversing/contacting the same separatory membrane during a stage of return of the cellular phase to the donor, said return of cellular phase to the donor being carried out without providing any blood pumping means intermediate said membrane-containing module and a container for the blood fraction which has traversed said membrane without being transported thereacross.

Another object of this invention is a specially adapted process/apparatus permitting a plasma of very high quality to be obtained under the best filtration yield conditions, while ensuring that there is virtually no haemolysis of the blood.

Another object of the invention is process/apparatus permitting the pressure of the cellular fraction exiting an upstream compartment of the membrane-containing module to be regulated to values generally ranging from 0 to 20 mm of mercury in relative pressure, the downstream compartment being at atmospheric pressure. Thus, a corollary object of the invention is process/apparatus which assures that the pressure of any liquid circulating in contact with the membrane does not exceed a specified predetermined value.

Another object of the present invention is process/apparatus permitting about 600 ml of plasma to be withdrawn from a donor in about 45 minutes and even in less time.

Yet another object of the present invention is process/apparatus for withdrawal of plasma in which it is possible to easily adapt operational strategy to the needs of the donor, the wishes of the operator and the characteristics of the membrane-containing module utilized.

Still another object of the present invention is process/apparatus allowing a yield per session which is greater than the intrinsic yield of the membrane-containing apparatus. By "yield per session" there is intended the ratio of the flow rate of liquid which has been transported across the membrane (i.e., the plasma) to the flow rate of blood withdrawn from or restored to the blood vessel of the donor. By "intrinsic yield" of the membrane-containing apparatus there is intended the ratio of the flow rate of filtered plasma to the flow rate of the blood upon entry into the membrane-containing module.

Another object of this invention is process/apparatus permitting the blood to be circulated in contact with the membrane at a flow rate which is higher than that of the blood withdrawn from the donor.

Another object of the present invention is process/apparatus in which the volumes of blood in circulation outside the body are small.

And still another object of this invention is process/apparatus equally well adapted to plasmapheresis with restoration to the patient, during the reinjection (or return) phase, of a replacement liquid corresponding in volume to that of the plasma withdrawn.

Briefly, the present invention features process/apparatus permitting body fluid withdrawal from a subject, human or animal, by inserting a needle only once, of a liquid which is circulated into contact with the membrane(s) of a module containing semi-permeable membrane(s) during a phase referred to as the withdrawal phase, the said liquid which contacts the membrane being separated into a fraction which is transported across the membrane and a fraction which is not transported across the membrane; and to then cause the fraction of the withdrawn liquid which has not been transported across the membrane to be returned to the patient during the phase referred to as the return phase, while again contacting the same membrane to effect a second separation thereof, but while circulating in the reverse direction.

Accordingly, provided hereby is improved plasmapheresis apparatus comprising, with reference to the several Figures of Drawing more fully described hereinbelow:

(i) a device 1 for injection into and withdrawal of body liquid from a subject;

(ii) a module 2 containing a semi-permeable membrane separating this liquid into a fraction which has been transported across the membrane and a fraction which has not been transported across the membrane, said module comprising an upstream compartment 3 and a downstream compartment 4 separated by the membrane;

(iii) a conduit 5 operably connecting the withdrawal device 1 to an inlet 6 into the upstream compartment 3 of the membrane-containing module 2;

(iv) a pump 7 situated along the conduit 5, said pump being capable of rotating (operating) in both directions;

(v) a pressure sensor 14 monitoring the liquid circulating in the conduit 5, said sensor being situated between the pump 7 and the inlet 6 into the upstream compartment 3 of the module 2;

(vi) a second conduit 16 operably connecting the outlet 15 from the upstream compartment 3 of the membrane-containing module 2 to a flexible container 17 for collection of the fraction of the liquid which has not been transported across the membrane;

(vii) a container 20 for collection of the liquid which has been transported across the membrane, this container 20 being in communicating relationship with the outlet of the downstream compartment 4 of the membrane-containing module 2;

(viii) means for monitoring the volume of liquid withdrawn from the subject during each withdrawal phase;

(ix) an inflatable flexible bag 18 exerting pressure, when inflated, upon the flexible container 17 thus enabling the return to the subject of the liquid contained in said container 17 during the phase referred to as the return phase;

(x) means for ensuring that the flexible bag 18 is not inflated beyond a certain predetermined pressure during the phase referred to as the return phase; and (xi) means 23 and 19 for inflating or deflating the said flexible bag 18.

Also featured hereby is improved process utilizing the aforedescribed apparatus, notably during a plasmapheresis procedure in which a subject donates his plasma.

BRIEF DESCRIPTION OF THE DRAWINGS

FIG. 3 is a schematic/diagrammatic illustration of another embodiment of process/apparatus according to the present invention.

DETAILED DESCRIPTION OF THE INVENTION

Figure 1:
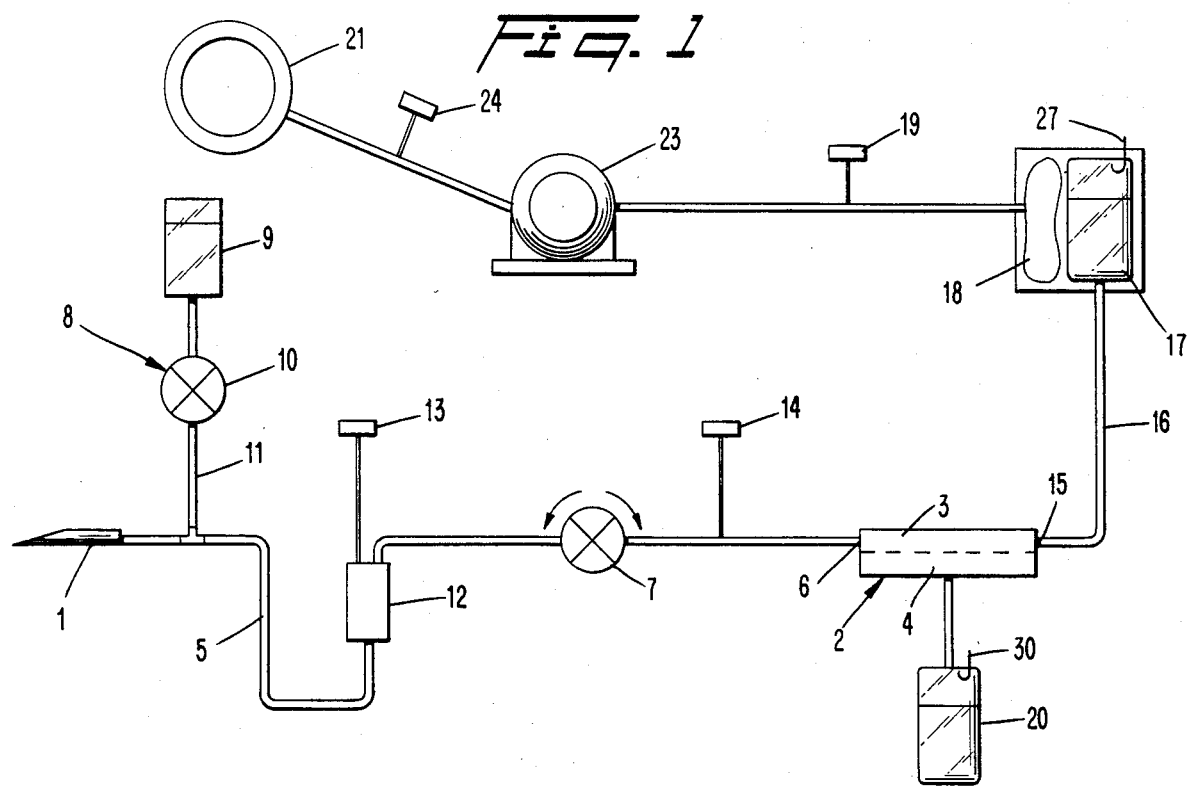
FIG. 1 is a schematic/diagrammatic illustration of one embodiment of the process/apparatus according to the present invention.

More particularly according to the present invention, with reference to the accompanying non-scale Figures of Drawing, in FIG. 1 there is depicted apparatus, especially adapted for donor plasmapheresis, comprising a device 1 for withdrawal of blood from the donor, advantageously a blood sampling needle. As exemplary, the needle can have an external diameter of 1.65 mm and an internal diameter of 1.45 mm, such as those indexed in blood transfusion centers under the designation 16 G. A module 2 containing a semi-permeable membrane, and comprising an upstream compartment 3 and a downstream compartment 4, operably communicates with the needle 1 via a conduit 5 extending from said needle 1 to a tubulure or inlet 6 which is in communication with the upstream compartment 3 of the membrane-containing module. This conduit 5 typically consists of plastic tubing, made, for example, of polyvinyl chloride. Along this conduit or line 5 is situated a pump 7 which can rotate or operate in both directions, advantageously a peristaltic-type pump. Between the pump 7 and the needle 1 is situated a device 8 adapted to transfer an anticoagulant into the blood flowing from the donor, for example, a glucose solution containing 35.6 g/liter of trisodium citrate, trademark AB 16 of Bieluz Co. This device 8 comprises, for example, a reservoir 9 of anticoagulant, a conduit 11 joined to the conduit 5 and the reservoir 9, and a pump 10, for example a peristaltic pump, situated along the conduit 11. This conduit 11 is joined to the conduit 5 as close as possible to the needle 1. Between the point of junction of the conduits 11 and 5 and the pump 7, a bubble detector or trap 12 and a pressure sensor 13 are advantageously situated in the conduit 5. The tubulure or outlet 15 of the upstream compartment 3 of the membrane-containing module 2 is connected by a conduit 16 to a flexible container 17, or bag, for collection of the blood which has been circulated across the membrane without being transported therethrough, such container 17 being, for example, a flexible plastic bag. This conduit 16 can be made from the same material and be of the same diameters as the conduit 5. The downstream compartment 4 of the module 2 communicates with a container 20 for collection of the plasma which has been transported across the membrane, this container 20 being, for example (like the container 17), a closed bag made from a flexible plastic material, the opposite sides of which are in contact with each other when the bag is empty, and which are separated from each other when a liquid penetrates into or fills same under very low pressure. Such bags 17 and 20 are marketed by the Fenwal Company under the trademark "transfer-pack" R 2022. The subject apparatus includes means, for example electronic balances 27 and 30, for detecting and monitoring the precise amounts contained in the containers 17 and 20.

The embodiment of FIG. 1 additionally includes a tourniquet 21, known per se, and means also per se known, for example, a compressor 23 for inflating it to the desired pressure when required, and a pressure sensor terminating inflation of the tourniquet 21 when a specified pressure is attained. The appartus shown in FIG. 1 also includes an inflatable bag 18 which can be inflated by the compressor 23 to the desired pressure by virtue of the pressure sensor 19, said inflatable bag transmitting and exerting pressure upon the container 17 which is adjacent to it, by means of, for example, a rigid transparent envelope which contains both the bag 18 and the flexible container 17.

Figure 2:
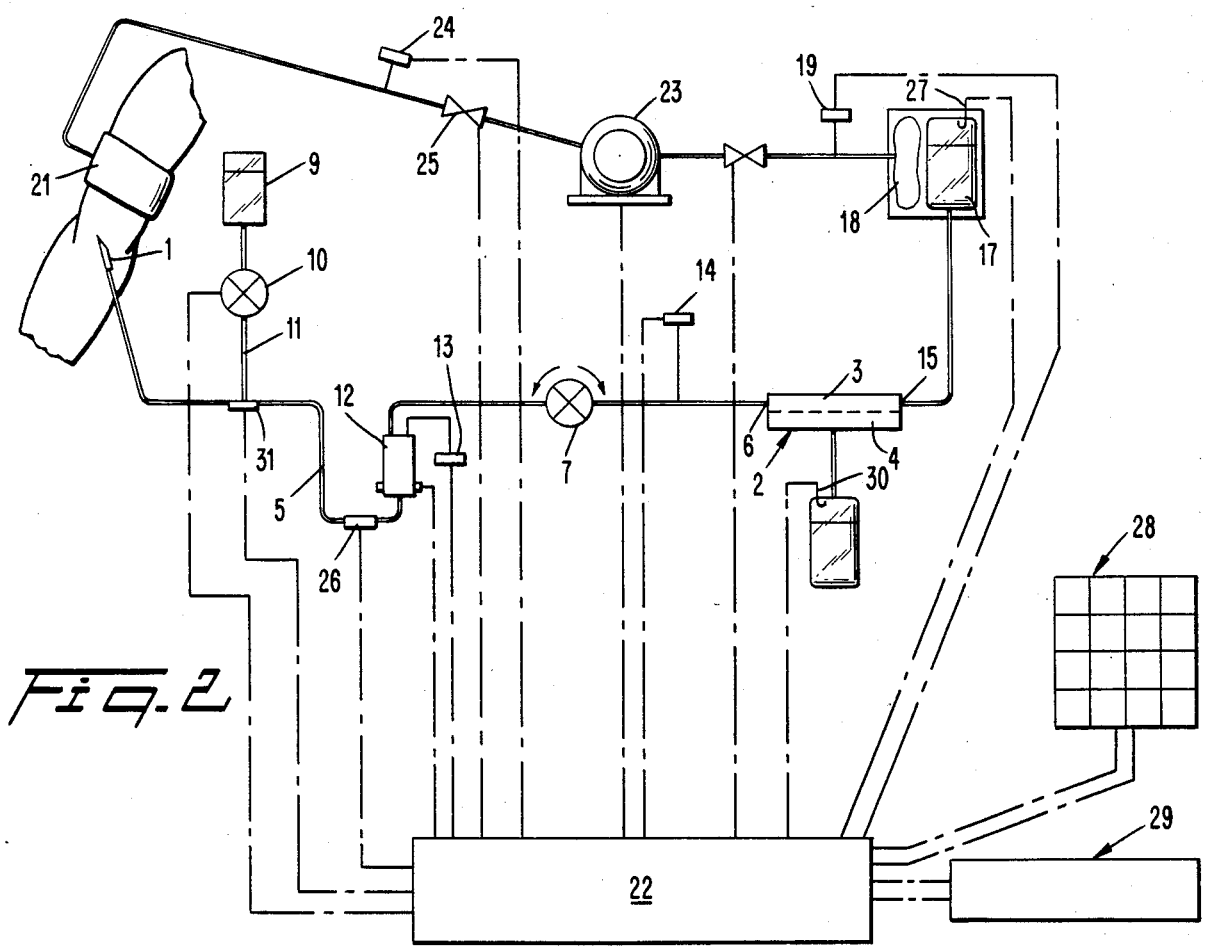
FIG. 2 is another representation of the process/apparatus of FIG. 1 to which have been added various means, devices and connections for process monitoring and control.

FIG. 2 represents an embodiment equivalent to that according to FIG. 1, but in which are shown the electrical connections of the different components to a logic unit 22 for control and monitoring, the electrical leads being represented by dashed lines. The unit 22 is connected to a current source (not shown). Naturally, all of the components of the subject apparatus can be consolidated on a console (or desk) having castors, for example, to facilitate shifting. The description of the logic unit 22 and also of the keyboard 28 and display unit 29, referred to hereinbelow, is not described herein in great detail, since the creation of the electrical circuits and advantageous utilization of microprocessors and memories would be apparent to the technician once the problem in question has been considered, i.e., after the technician has been requested to arrange that the apparatus described should function automatically and reliably. The embodiment of FIG. 3 is likewise advantageously connected in the same manner to a logic unit 22 for control and monitoring (not shown).

The module 2, above described, can comprise a membrane in flat or planar form, in spiral form, or in the form of small fine tubes such as hollow fibers. When the membrane comprises a plurality of hollow fibers, the blood advantageously circulates inside the hollow fibers, the combined interior volumes of the fibers constituting the upstream compartment 3 of the module. When the membrane is in flat or spiral form, the blood advantageously circulates between a pair of membranes or series of pairs of membranes, which constitute the upstream compartment 3 of the membrane-containing module 2.

The membranes used for plasmapheresis procedures are preferably those which permit the collection of a plasma: in which all of the proteins of the original blood are again found in the same proportions, the protein concentration of which is greater than 55.5 g/liter, in which there are no red cells and in which the concentration of platelets is less than 15,000 platelets per $mm^3$. The membranes selected are those which also permit no haemolysis of the blood circulating in contact therewith, while at the same time providing good filtration yields.

These plasmapheresis membranes advantageously have a rejection coefficient for latex of less than 75% for latex particles calibrated at 0.27 microns, and a rejection coefficient for latex of greater than 15% for latex particles calibrated at 0.64 microns. Preferably, the rejection coefficient for latex particles calibrated at 0.27 microns is less than 30%, and the rejection coefficient for latex particles calibrated at 0.64 microns is greater than 90%.

To carry out the aforenoted measurement of rejection coefficient for latex, the following procedure is adopted, when the membranes are flat.

50 ml of suspension of calibrated polystyrene particles of diameter 0.27–0.4 or 0.64 microns (marketed by Rhone-Poulenc under the trademark ESTAPOR) diluted to 0.1% with distilled water, with addition of 1% surfactant (alkylarylsulfonate, trademark SINOZON NAS 60, of the Sinnova Company), are loaded into a cell of type Amicon Model 52.

The Amicon cell is fitted with a sample of the membrane supported on a mesh. An air pressure corresponding to 20 cm of water is established. The first six milliliters of filtrate are recovered for determination of the concentration (cf) of the calibrated particles.

The rejection coefficient is defined by the formula:

$$\frac{(0.1 - cf) \times 100}{0.1}$$

Membranes having the above characteristics are generally of synthetic material, for example, cellulose esters (cellulose nitrate and the like) regenerated cellulose, polycarbonate and the like. These membranes can also be based on polyetherurethanes containing heparinized ammonium groups, or be of acrylonitrile copolymer. These membranes are advantageously reinforced by a mesh when they are in the form of flat membranes, and advantageously have a thickness of from 50 to 200 microns.

The apparatus of FIGS. 1 and 2 is used as follows, for example, in the case of a donor plasmapheresis procedure. The conduit 11 is first filled with the citrate-containing solution, and since the junction between the conduit 11 and the conduit 5 is in point of fact very close to the needle 1, the latter may be considered to be at least in part filled with this citrate-containing solution. The tourniquet 21 having been previously inflated to the desired pressure (about 60 mm of mercury) by means of the compressor 23 in conjunction with the pressure detector 24 and the electromagnetic valve 25 (these latter two components being connected to the logic unit 22), the needle 1 is inserted into a vein of the donor after conventional preparation of the insertion site, which is situated between the tourniquet and the extremity of the selected limb. At this moment the pump 10 introduces citrate into the conduit 5, while the pump 7 rotates and conducts the donor's blood to the container 17 by way of and through the upstream compartment 3 of the membrane-containing module 2. The plasma fraction of the blood which is transported across the membranes enters the downstream compartment 4 which is connected to the bag 20. The pressure sensor 13 controls the pump 7 such that the pressure measured at this point in the line 5 always remains greater than a certain value, generally close to 0 mm of mercury, designated the threshold pressure, to ensure that the pump 7 does not "draw" the blood directly from the donor's vein. If the pressure in this part of the line becomes lower than the specified pressure fixed at the sensor 13, the logic unit 22 automatically operates and temporarily arrests or slows down the rotation of the pump 7, as long as the required pressure has not returned. The pressure sensor 14 is adjusted such that the pressure of the blood at the inlet 6 of the upstream compartment 3 is at a certain value, for example, from 40 to 100 mm of mercury in relative value, and preferably from 60 to 90 mm of mercury, and any pressure in excess thereof are automatically detected. The pump 7 rotates such that the pressure of the blood at the inlet of the upstream compartment 3 of the module 2 is as close as possible to the desired maximal pressure, but if this desired maximal value is exceeded, the logic unit 22 automatically arrests the pump 7. The pressure at the outlet 15 of the upstream compartment 3 of the membrane-containing separator 2 is from 0 to 20 mm of mercury in relative value, while the downstream compartment 4 is at atmospheric pressure.

The period during which the blood leaves the vein of the donor is called the withdrawal phase. The latter comes to an end, for example, according to the predetermined volume of blood desired to be withdrawn from the donor (in each withdrawal phase), this volume naturally always being less than the volume of the flexible container 17 for collection of the blood. Advantageously, a tachymetric device is operably associated with the pump 7, and when the desired volume of blood is withdrawn from the donor, the logic unit 22 operates and arrests the pump 7. The logic unit 22 then simultaneously activates the electromagnetic valve 25, such that the tourniquet 21 deflates and the pump 7 commences rotation in the opposite direction to that in the preceding phase, referred to as the withdrawal phase, terminates distribution of anticoagulant from the vessel 9, and pressurizes the inflatable bag 18 by means of the compressor 23 in conjunction with the pressure sensor 19 and an electromagnetic valve (not shown). The pressure in the inflatable bag 18, and thus that of the blood contained in the flexible container 17, is the same as that used before, during the withdrawal phase, at the inlet of the upstream compartment 3, i.e., from 40 to 100 mm of mercury in relative value. During this return phase, during which the pump 10 for supplying the anticoagulant is not operating, the blood in the flexible container 17 is subjected to a second separation in the membrane-containing module 2, entering the upstream compartment 3 through the "outlet" tubulure 15, and plasma is again collected in the container 20. During this return phase, the sensor 13 ensures that the pressure of the blood returning to the donor does not exceed a certain maximal specified value, while operating as close to this value as possible. If this maximal pressure value is exceeded, for example through obstruction of the needle, the sensor 13 actuates the pump 7 which is controlled thereby, and the logic unit arrests the pump 7. The sensor 14 ensures that the outlet pressure of the upstream compartment 3 is the desired pressure, i.e. in the region of zero mm of mercury. If this pressure is greater than the desired specified pressure, the pump 7 controlled by the sensor 14 is accelerated in its rotation, provided that the maximal pressure of the sensor 13 is not attained; otherwise this sensor 14 enables the pressure of the inflatable bag 18 to be affected, by causing the bag to slightly deflate. If, during the phase of return to the donor, bubbles are detected by the detector 12, the logic unit 22 immediately arrests the pump 7 and, if necessary, actuates a clamp 26, or similar obstruction device, which closes the conduit 5. The blood can, if necessary, pass through a conventional filter provided in the bubble detector 12, to avoid the possibility of returning undesirable particles to the donor. This filter can, for example, be moved aside during the withdrawal phase, returning to a seating provided in the bubble detector during the return phase. The completion of the return phase is detected by, for example, an optical detector 27 provided along the conduit 5. When there is no further blood (deprived of a fraction of its plasma) passing the point where the detector 27 is situated, the logic unit 22 intervenes to terminate the return phase and cause the apparatus to convert back into withdrawal mode. Thus, the pump 7 is arrested, and set in motion to rotate in the opposite direction to that in the return phase, while the tourniquet 21 is again inflated, the pump 10 supplying citrate again actuated and the flexible bag 18 deflated. When, upon completion of a particular return phase, it is seen that the plasma bag 20 contains overall sufficient amount of plasma, the procedure is terminated completely.

The flow rate of the pump 10 is generally adjusted such that, during the phase referred to as the withdrawal phase, one volume of citrate is used for 8 volumes of blood, or preferably 1 volume of citrate for 16 volumes of blood, the ratio being selected by the operator. This dilution ratio is advantageously obtained by placing the speed of rotation of the pump 10 under the control of that of the pump 7.

It will, thus, clearly be seen that the apparatus according to the present invention can be made the subject of highly elaborate automation. Thus, as is shown more especially in FIG. 2, the logic unit 22 for control and monitoring can be connected to a keyboard 28 and a display unit 29. Likewise, the logic unit 22 can be connected to a synoptic chart (not shown) on which the localization of any anomalous functioning is indicated to the operator by a warning light, at the same time that, for example, an audible signal is emitted. On the keyboard 28 it is possible to choose the maximum volume of blood desired to be circulated during the withdrawal phase (300, 350, 400, 450 cm$^3$ of blood, for example), by pressing the corresponding key. It is also possible to choose the volume of plasma desired to be withdrawn during the session (400, 500 or 600 cm$^3$, for example), by pressing the corresponding key. Thus, a device 30, for example, of electronic balance type, is advantageously associated with the plasma bag 20 to enable the volume (or weight) of plasma withdrawn to be known instantaneously as the session progresses, this device 30, known per se, being connected to the logic unit 22. On the keyboard 28, a key can also be provided for automatic priming of the line 11 before inserting the needle into the donor. By pressing this key, the pump 10 starts and stops automatically when the citrate solution is detected at, for example, the junction 31 of the two lines 11 and 5. On the keyboard 28, it is also possible to provide, for example, a key to show on the display unit 29 the instantaneous volume of plasma in the bag 20 at any moment, a key to show on the display unit 29 the flow rate of blood from the pump 7, to show the timing of the session in progress, and the like. The apparatus can include, in conjunction with the logic unit 22 and the values designated at the keyboard 28 regarding the volume of blood desired during the withdrawal phase and the total volume of plasma desired, an integration system operating during the last withdrawal phase such that the volume of blood withdrawn enables the total desired volume of plasma to be obtained upon completion of the last return phase.

Numerous variations of the apparatus described above will be apparent to one skilled in this art. By way of example, the apparatus can include a small, collapsible balloon in the line 5 between the junction 31 and the clamp 26. This small balloon then serves as a double security device with the pressure sensor 13, in the sense that it acts as a seal when the flow rate at the pump 7 is greater than that from the vein, if the sensor has not functioned during the withdrawal phase. This small collapsible balloon can, if required, be substituted for the sensor 13.

Likewise, the device 8 intended for introducing the anticoagulant can optionally be omitted, if the interior of the needle 1, bubble detector 12 and lines 5 and 16 are coated, for example, with a polymer based on polyether-urethanes containing heparinized ammonium groups, such as those described in particular in U.S. Pat. No. 4,046,725. The lines 5 and 16 can optionally comprise a polymer such as those described in the aforesaid '725 patent, or a mixture of polyvinyl chloride and polyether-urethane containing heparinized ammonium groups, such as in the mixtures noted in published European Patent Application No. 12,701. The microporous membrane can likewise be prepared from a mixture of polymers according to the said published European Patent Application No. 12,701.

With the apparatus such as depicted in FIGS. 1 and 2 and described above, plasmapheresis procedures have been performed on a donor, using, by way of example, a membrane-containing module 2 in which the total membrane area is 600 cm$^2$ and which contains two membranes arranged facing each other (forming the upstream compartment, 3) between which the blood circulates. Each membrane is 30 cm long and 10 cm wide and supported on a mesh, as described in more detail below. The average thickness of the blood film is 370 microns. The withdrawal device 1 is a needle of 1.65 mm external diameter and 1.45 mm internal diameter. The conduits 5 and 16 are made from polyvinyl chloride (PVC) and have an internal diameter of 3.5 mm. The conduit 11 is also made from PVC and has an internal diameter of 0.9 mm. The pump 10 is a peristaltic pump (trademark RP 04, marketed by Hospal Company), said pump comprising a pump body enveloped in silicone.

The pump 7 is a peristaltic pump (trademark RP 01, marketed by Hospal Company), said pump also comprising a pump body enveloped in silicone. The containers 17 and 18 have a capacity of 1000 cm$^3$ and are also made of PVC.

The sensor 13 is a National Semiconductor sensor trademark LX 1801 GB, in which the pressure registered is adjusted to 10 mm of mercury during the withdrawal phase and the maximal pressure value is adjusted to 100 mm of mercury during the return phase. The sensors 14 and 19 are sensors of the same make and same reference as the sensor 13. The sensor 14 is adjusted to a maximal relative pressure of 80 mm of mercury for the withdrawal phase, and for a minimal relative pressure of 10 mm of mercury during the return phase, while the sensor 19 is adjusted to a relative pressure of 80 mm of mercury for the return phase. Thus, the pressure of the blood in circulation is greater than the pressure of the plasma collected in the downstream compartment 4 of the membrane-containing module 2, which is at atmospheric pressure. The average pressure across the membrane is equal to:

$$(80+10/2)=45 \text{ mm of mercury.}$$

During each withdrawal phase, the tourniquet is inflated to 60 mm of mercury and the flow rate of citrated blood at the inlet of the separator is 85 ml/mm, on the average.

The membrane used is a membrane supported on a mesh, obtained from a solution of polymer in an organic solvent, the solution being permitted to flow onto a mesh rotating in contact with a belt having a very smooth surface. This solution contains 8% by weight of a copolymer of acrylonitrile/methyl methacrylate/sodium methallyl sulfonate, comprising 7.75% by weight of methyl methacrylate and 80 mEq/kg of acidic residue, dissolved in a mixsure of N-methylpyrrolidone/glycerin (70.8/21.2%). This copolymer has a specific viscosity of 0.3 at 20° C. in dimethylformamide solution at a concentration of 2 g/liter.

The mesh used is a monofilament fabric of ethylene glycol polyterephthalate, having a mesh of 75 microns, the thread diameters being 55 microns and the open or voids area being 33%. This mesh weighs 55 g/m$^2$.

The microporous membrane which is obtained, supported on the mesh, has a thickness of 120 microns, and its mass is 10 g of polymer per m$^2$ of dry membrane.

The microstructure of the polymer phase of the membrane is porous and regular. Its porosity is 80%, the porosity being defined as the ratio (multiplied by 100) of the volume of the pores to the total volume of the membrane (polymer+pores).

The flow rate for water (with 1% of a surfactant added) of this membrane supported on the mesh is 4.5 ml/h cm$^2$ mmHg.

The rejection coefficient for latex of this membrane is:

(i) 5 to 15% for latex calibrated at 0.27 microns,
(ii) 65 to 80% for latex calibrated at 0.4 microns,
(iii) 98 to 100% for latex calibrated at 0.64 microns.

With the apparatus as defined above, fixing the volume of blood at 350 cm$^3$ during the withdrawal phase, the total volume of plasma to be collected at 600 cm$^3$, and the ratio of the volume of anticoagulant solution/volume of blood at 1/16, during each withdrawal phase, the plasmapheresis procedure was completed in 44 minutes after having performed 6 withdrawal phases and 6 return phases.

The plasma collected is practically acellular. It contains no contamination by red cells and only 3,000 platelets per mm$^3$. The protein concentration of the plasma is 57 g/liter.

The embodiment of FIG. 3 is a variant of that illustrated in FIG. 1 and comprises the same components as described above, and, in addition, a conduit 16b operably communicating the flexible container 17 with the line 5, generally at a point (A) situated between the pump 7 and the bubble trap 12. This embodiment also includes a second inflatable bag 18b exerting pressure upon the flexible container 20 to transmit the desired pressure to the liquid contained in this container 20 during each return phase, such pressure advantageously being the same in the bags 18 and 18b. The presence of the sensor 13 is, however, optional in this embodiment of FIG. 3.

The embodiment of FIG. 3 has the advantage over that of FIG. 1, described above, of permitting a recirculation of the blood, at a greater speed than its speed of withdrawal or return, in the loop defined by the upstream compartment 3 of the membrane-containing module 2, the conduit 16, the flexible container 17, the conduit 16b, and the portion of the conduit 5 between the point A and the tubulure or inlet 6 of said membrane-containing module 2. Thus, the yield per session, for example of plasmapheresis, is greater than the intrinsic yield of the apparatus.

To use the apparatus shown in FIG. 3, the procedure is as follows, for example, in the case of a donor plasmapheresis session. The needle 1 is first inserted into a vein of the donor according to the same protocol as described for the embodiment of FIG. 1, after the tourniquet 21 has been inflated to the desired pressure (for example, 60 mm of mercury), but the pump 7 is not started until a volume Vo of blood has been attained in the flexible container 17. Thus, the blood passes first through the conduit 5 to the junction A (point A), then through the conduit 16b, with the pump 10 comprising the anticoagulant device functioning as described for the embodiment of FIG. 1. When this volume (Vo) is attained the pump 7 is started such that the blood enters into the upstream compartment 3 of the membrane-containing module 2 through the tubulure or inlet 6. The pressure sensor 14 enables the greatest possible pressure across the membrane to be selected without haemolysis occurring, the pressure across the membrane at the outlet 15 of the upstream compartment 3 being approximately equal to 0 mm of mercury. Typically, the pressure across the membrane at the inlet of the membrane-containing module 2 ranges from 40 to 100 mm of mercury. If the predetermined pressure is exceeded, the sensor 14 acts on the pump 7, which is under its control, to slow it down or arrest it temporarily. During this withdrawal phase, the flexible containers, 17 for collection of the blood which has circulated in contact with the membrane without being transported thereacross, and 20 for collection of the plasma, are approximately at atmospheric pressure. During this withdrawal phase, the blood coming from the donor is withdrawn as in the conventional taking of blood samples, since the pump 7 does not draw it directly, but rather acts on the blood in the container 17. When the desired predetermined quantities of blood and plasma have been collected in the bags 17 and 20, this being ascertained, for example, by means of electronic balances 27 and 30, the withdrawal phase is then terminated, such that a return phase may be begun. The tourniquet 21 is then deflated, the pump 10 is arrested, the inflatable bags 18 and 18b are both inflated to a pressure corresponding to that of the entry pressure of the blood in the membrane-containing module 2 during the withdrawal phase, the pump 7 continues to rotate in the same direction, and the specified pressure at the sensor 14 is increased in comparison with that in the withdrawal phase by the pressure of the bags 18 and 18b, such that the pressure across the membrane is the same during the return phase as during the withdrawal phase. When the volume (Vo) is attained in the container 17, a withdrawal phase is then recommenced as described above, by pressurizing the tourniquet, deflating the bags 18 and 18b, starting the pump 10 and lowering the specified value of the entry pressure of the blood in the upstream compartment 3 of the membrane-containing module 2, the pump 7 continuing to rotate in the same direction. Completion of this second withdrawal phase will be reached when the volume outside the body corresponds, for example, to the volume of the blood in the container 17 plus the volume of the plasma in the container 20, minus the known volume of plasma collected in bag 20 during the first withdrawal phase. It should be noted that during each withdrawal phase in the embodiment of FIG. 3, the pump 10 for distribution of the anticoagulant is no longer under the control of the pump 7, but advantageously is controlled by the volume of blood collected in the container 17.

The apparatus as above described can very obviously be used with animals (dog, horse, etc.), in particular for plasmapheresis procedures.

Generally, the subject apparatus can be used every time it is desired to insert a needle into a subject (human or animal) at only one single site, using a simple needle (having only one internal channel), and to cause the withdrawn liquid from the subject, generally blood, to circulate first in one direction (withdrawal phase) and then in the opposite direction (return phase) in contract with a semipermeable membrane comprising a membrane-containing separator having means for controlling the desired pressures of the blood at the inlet and outlet of said membrane-containing separator, during both phases. Thus, with this apparatus it is possible to eliminate components of the blood in circulation, a first time during the withdrawal phase, and a second time during the return phase, during which the fraction of the blood which has not been transported across the membrane is restored to the subject.

Thus, the apparatus described above can be used for applications other than donor plasmapheresis. According to the separation characteristics of the semipermeable membranes used, it will be possible to deplete the circulating blood of only certain of its proteins or certain constituent components of the plasma. It is also possible to perform haemofiltration sessions, conditional on, for example, the reinjection of a replacement liquid controlled by the quantity of filtered liquid collected in the container 20.

This subject apparatus can also be used for plasma exchange procedures, i.e., by reinjecting into the patient, during the return phase, a plasma equivalent in quantity to that withdrawn, by means of a pump and conduit (not shown) attached, for example, to the conduit 5 between the bubble detector 12 and the pump 7. If the patient has an arterio-venous shunt, it is not necessary to use the tourniquet 21.

The apparatus according to the present invention can also be used for the treatment of the ascites fluid of a patient, there being no need in this application for the tourniquet, the device 8 for distribution of the anticoagulant, or the bubble detector 12.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. Apparatus for processing body fluids, comprising (i) needle means for withdrawing and returning body fluid from and to a living patient, (ii) a body fluid separating module which comprises a first compartment, a second compartment and a semipermeable membrane disposed between said first and second compartments, said semi-permeable membrane being permeable to a liquid fraction of the body fluid, said second compartment being adapted to receive liquid fraction which permeates through said semi-permeable membrane from said first compartment, (iii) first passage means communicating said needle means (i) with a first end of the first compartment of said separating module (ii), (iv) first pumping means provided at a location along said first passage means for pumping body fluid in either direction through said first passage means, (v) first sensor means for monitoring pressure of the body fluid circulating in said first passage means (iii) at a location between said pumping means (iv) and the first end of the first compartment of said separating module (ii), (vi) second passage means communicating a second end of the first compartment of said separating module (ii) with (vii) flexible container means, (viii) means for collecting from the second compartment liquid fraction received by the second compartment, (ix) second sensor means for monitoring the amount of body fluid withdrawn from the patient, and (x) means for expelling body fluid from said flexible container means (vii) to return at least a portion of body fluid withdrawn to said flexible container means to the patient.

2. The apparatus as defined in claim 1, further comprising means for limiting pressure of body fluid being returned to the patient to a peredetermined value.

3. The apparatus as defined in claim 2, wherein said expelling means (x) comprises an inflatable flexible bag and means for inflating and deflating said flexible bag.

4. The apparatus as defined in claim 1, further comprising an inflatable tourniquet, means for inflating said tourniquet upon withdrawal of body fluid from the patient and means for deflating said tourniquet upon return of body fluid to the patient.

5. The apparatus as defined in claim 1, further comprising means for introducing an anticoagulant into the body fluid during withdrawal of body fluid from the patient.

6. The apparatus as defined in claim 1, further comprising means responsive to said second sensor means for reversing operation of said pumping means (iv) when the amount of body fluid in said flexible container means equals a predetermined value.

7. The apparatus as defined by claim 1, further comprising means to monitor completion of a phase of return of body fluid to the patient, and means to ensure conversion to a phase of withdrawal of body fluid from said patient.

8. The apparatus as defined in claim 1, further comprising third sensor means for monitoring the amount of liquid fraction collected by said collection means (viii).

9. The apparatus as defined in claim 1, further comprising a body fluid bubble trap at a location along said first passage means (iii) between said pumping means (iv) and said syringe means.

10. The apparatus as defined in claim 1, further comprising logic circuitry means for the automatically controlling and monitoring said apparatus.

11. The apparatus as defined in claim 1, further comprising means for maintaining pressure of the body fluid in said first passage means (iii) during the withdrawal of body fluid from the patient above a predetermined value.

12. The apparatus as defined in claim 2, whereby at least a portion of the body fluid contained in said flexible container means (vii) is returned to the patient reversibly along the same path as taken during the withdrawal thereof.

13. The apparatus as defined in claim 1, further comprising means for maintaining pressure of body fluid in said first conduit means (iii) during return of body fluid to the patient below a predetermined value.

14. The apparatus as defined in claim 1, further comprising third passage means communicating said flexible container means (vii) with said first passage means at a location along said first passage means between said pumping means (iv) and said needle means.

15. The apparatus as defined in claim 14, wherein said container means (vii) and said collecting means (viii) each comprise a flexible bag.

16. The apparatus as defined in claim 15, further comprising means for subjecting said container means (vii) and said collecting means (viii) to generally equal pressure, whereby pressures at both sides of said membrane may be maintained generally equal during return of body fluid to the patient.

17. The apparatus as defined in claim 16, further comprising means for maintaining pressure across the membrane separating module approximately the same during both withdrawal of body fluid from the patient and return of body fluid to the patient.

18. A plasmapheresis process comprising the steps of withdrawing body fluid from a living patient through a first passage and through a compartment at least partially defined by a semipermeable memberane, simultaneously with said withdrawing step, separating a liquid fraction from said withdrawn body fluid with said semipermeable membrane, collecting at least a portion of the remaining fraction of said body fluid in a flexible container and returning to the patient at least a portion of the remaining fraction of body fluid along a return path including said compartment by directing pressure against said flexible container to expel body fluid therefrom, said returning body fluid to the patient at the same location on the patient as in the withdrawing step.

19. The process as defined in claim 18, further comprising the step of recirculating at least a portion of the withdrawn body fluid along a recirculation path including said compartment and said flexible container during said withdrawing and returning steps.

20. A plasmapheresis process comprising the steps of:
inserting a needle into a vein of a living patient and applying a tourniquet to the living patient;
withdrawing blood through the needle, through a first passage and through a compartment of a separator apparatus by operating a pump operatively connected to said first passage, said first passage communicating a first end of said compartment to said needle, said separator apparatus including a membrane at least partly defining said compartment, said membrane being permeable to a plasma fraction of the blood, at least a portion of the plasma fraction permeating through said mmebrane as blood passes through said compartment;
operating a device for distributing anticoagulant and a bubble trap at respective locations along said first passage during said withdrawing step;
regulating the pump with a first sensor adapted to monitor pressure in said first passage at a location between said needle and said pump so as to prevent the pump from withdrawing blood at pressure below blood pressure in the vein at the needle;

regulating the pump during said withdrawing step with a second sensor adapted to monitor pressure in said first passage at a location between said pump and said first end of the compartment so as to maintain pressure of blood at said first end of said compartment at a pressure generally equal to but not greater than a first predetermined value;

collecting the blood which has passed through the compartment in a flexible, first container;

collecting plasma fraction which has permeated through the membrane of the separator apparatus in a second container;

terminating the withdrawing step when a predetermined amount of blood has been collected in the first container;

after said terminating step, performing a return phase which includes the steps of deflating the tourniquet, arresting the device for distributing anticoagulant, operating the pump in reverse, and returning at least a portion of the blood collected in the flexible, first container reversibly through said first compartment of said separator apparatus, said returning step including exerting pressure on the first container by inflating a first inflatable bag adjacent the first container;

during the return phase, controlling the pump with the first pressure sensor, so that blood returning to the donor is at a pressure below a second predetermined value while simultaneously controlling the pump with the second sensor so that the pressure at the first end of the compartment of the separator apparatus is approximately equal to atmospheric pressure;

terminating the return phase when the first container has been emptied by a predetermined amount;

repeating the withdrawing step and return phase alternately until a desired quantity of plasma fraction is obtained in the second container.

21. The plasmapheresis process as defined in claim 20, wherein said second container is flexible and during said return phase pressure is exerted on the second container by inflating a second inflatable bag adjacent the second container, the pressure exerted upon the first and second containers being generally equal, whereby pressure across said membrane during said withdrawal and return phases may be maintained generally equal.

22. The plasmapheresis process as defined in claim 20, wherein said first predetermined value is selected such that pressure at a second end of said compartment is approximately equal to atmospheric pressure.

23. A plasmapheresis process comprising the steps of:

inserting a needle into a vein of a living patient and applying a tourniquet to the living patient;

withdrawing blood through the needle, through a first passage and into a flexible first container;

during at least a portion of said withdrawing step, continuously circulating blood in a direction along a circulation path from said first container through a first compartment of a separator apparatus and back to said first container by operating a pump at a location along said path, said first passage communicating said needle with said circulation path, said separator apparatus including a membrane at least partly defining said compartment, said membrane being permeable to a plasma fraction of the blood, at least a portion of the plasma fraction permeating through said membrane as blood passes through said compartment;

operating a device for distributing anticoagulant and a bubble trap at respective locations along said first passage during said withdrawing step;

regulating the pump with a first sensor adapted to monitor pressure in said circulation path at a location between said compartment and said pump so as to maintain pressure of blood at a first upstream end of said compartment generally equal to but not greater than a first predetermined value;

during said withdrawing step, collecting plasma fraction which has permeated through the membrane in a flexible second container, whereby in a withdrawal phase, blood is drawn from the living patient and is circulated in contact with the memberane of the separator apparatus by operation of the pump;

terminating the withdrawal phase and starting a return phase when a predetermined maximum amount of blood is obtained in the first container, the return phase including the steps of deflating the tourniquet, arresting the device for distribution of anticoagulant, subjecting the first and second containers to generally equally pressure in the range of 20 and 100 mm of mercury by inflatable bags while operating the pump in the same direction as during the withdrawal phase to circulate blood along said circulation path while blood is being returned to the living patient, and terminating the return phase when blood in the first container equals a predetrmined minimum value; and repeating the withdrawal phases and return phases until a desired amount of plasma fraction is collected in the second container.

* * * * *